United States Patent [19]

Gonser

[11] Patent Number: 4,836,782
[45] Date of Patent: Jun. 6, 1989

[54] METHOD FOR PROVIDING DIRECT COOL BEAM INCIDENT LIGHT ON DENTAL TARGET

[75] Inventor: Donald I. Gonser, York, Pa.

[73] Assignee: Dentsply Research & Development Corp., Milford, Del.

[21] Appl. No.: 492,286

[22] Filed: May 6, 1983

[51] Int. Cl.[4] .................... A61C 5/00; A61C 3/00
[52] U.S. Cl. ........................................ 433/229; 433/25
[58] Field of Search ................... 433/229, 141, 25; 362/32, 109, 283, 204; 350/96.10, 96.18, 96.28

[56] References Cited

U.S. PATENT DOCUMENTS

| | | | |
|---|---|---|---|
| 624,392 | 5/1899 | Smith | 350/96.10 X |
| 1,542,183 | 6/1923 | Steinberg | 350/96.10 X |
| 2,077,102 | 4/1937 | Fardon | 350/96.10 X |
| 2,945,958 | 7/1960 | Morris | 250/230 |
| 3,539,798 | 11/1970 | Perry | 362/253 X |
| 3,596,083 | 7/1971 | Lovering . | |
| 3,624,834 | 11/1971 | Malifaud | 350/116 |
| 3,638,312 | 2/1972 | Szwarc et al. | 433/25 |
| 3,660,088 | 5/1972 | Lundsager . | |
| 3,712,984 | 1/1973 | Lienhard | 250/504 |
| 3,753,720 | 8/1973 | Klocsewski . | |
| 3,868,513 | 2/1975 | Gonser | 433/228 |
| 4,149,086 | 4/1979 | Nath | 250/504 |
| 4,298,806 | 11/1981 | Herold | 250/504 |
| 4,436,806 | 3/1984 | Rendulic et al. . | |
| 4,445,858 | 5/1984 | Johnson | 433/229 |
| 4,666,405 | 5/1987 | Ericson | 433/229 |
| 4,666,406 | 5/1987 | Kanca, III | 433/229 |

FOREIGN PATENT DOCUMENTS

| | | | |
|---|---|---|---|
| 305899 | 7/1961 | Fed. Rep. of Germany . | |
| 2901534 | 7/1979 | Fed. Rep. of Germany | 433/229 |
| 2841112 | 4/1980 | Fed. Rep. of Germany | 633/141 |
| 2341815 | 10/1977 | France | 433/141 |

Primary Examiner—Robert Peshock
Attorney, Agent, or Firm—Woodcock, Washburn, Kurtz, Mackiewicz & Norris

[57] ABSTRACT

Apparatus is provided for generating a condensed beam of light having a limited degree of scatter, or deviation, comprising light collimating means for providing a source of collimating light and light condensing means operatively connected to the collimating means, such as a truncated cone with a reflective inner surface, the condensing means providing a light beam output having a light divergence limited to about 30° or less. The low divergence beam generating apparatus might be incorporated into larger dental apparatus which can be operator manipulated to provide different modes of light output, which modes include the condensed beam with and without a bandpass of visible wavelengths. In practicing the method of this invention, particularly with respect to dental applications such as curing restorative materials placed in one or more teeth of a patient's oral cavity, the low divergence beam is directed at the teeth from a distance of about 1 cm, enabling reduced operator dependence in the process of curing the restorative materials.

11 Claims, 4 Drawing Sheets

METHOD FOR PROVIDING DIRECT COOL BEAM INCIDENT LIGHT ON DENTAL TARGET

BACKGROUND OF THE INVENTION

1. Field of the Invention

This invention relates to apparatus, and the corresponding method for visible light curing of dental targets such as restorative materials placed in teeth, and in particular an apparatus and method for providing and using a relatively low divergence collimated beam of light which is non-contact applied to the dental target.

2. Background of the Invention

In the field of dentistry, photo-curable compositions have been used to produce dental sealents, dental filling materials, dental adhesives and the like. In a first generation of such applications, the restorative materials were curable by the application of ultraviolet radiation. In order to provide such UV radiation, dental guns and other forms of apparatus for producing concentrated beams of UV radiation were provided. See, for example, the prior U.S. Patents to Gonser, U.S. Pat. Nos. 4,112,335 and 4,229,658, assigned to the same assignee. However for many applications, including the dental area, it was found that visible light curable compositions were preferred. Visible light is more efficient in crossing the boundary between dissimilar materials, through normal tooth structure, and through materials which have already been cured. Accordingly, apparatus for producing concentrated visible light was produced and made available for dental applications. See the Gonser U.S. Pat. No. 4,385,344, "Visible Light Apparatus For Curing Photo-Curable Compositions", assigned to the same assignee.

The use of visible light curing techniques in the dental field has become relatively widespread, but at the same time certain limitations have been observed. The apparatus that has been available in the art produces a light output which is relatively divergent, e.g. the beam may diverge at about 30° from the beam axis. It is known from the physical laws that light is directed at tooth structure will scatter as a function of the angle of incidence. The greater the divergence of the light flux from a path directly normal to the tooth surface, the greater the degree of scatter, and thus reduced penetration into the tooth structure. In prior art apparatus, a great deal of the light output is found to scatter, such that is does not penetrate into the light sensitive material placed in a tooth cavity. This characteristic of prior art light sources leads to relative inefficiency and unreliability for photocuring restorative materials that are either thick (>2 mm) or located behind natural tooth structure, such as in situations where the light cannot be directly applied to light sensitive materials.

Another feature of prior art light sources, particularly for dental applications, is that they provide very condensed small area light outputs. Since the light diverges at a great angle, it is necessary for the operator to position the output directly on the light sensitive restorative material, i.e. the tip end of the light output must make contact with the restorative material or the tooth structure. As a result of this requirement, the procedure of photocuring has been very operator dependent, since the dentist or dental technician must position the light precisely at the proper position. If the target area to be cured presents a cross section which is substantially larger then the cross section of the light output, then the operator must take great care to manipulate the contact point or light output aperture so as to achieve light penetration into all applicable areas where all of the restorative material must be photocured. Thus, it has been seen that there are instances where incomplete curing has resulted. Undercured zones of light polymerizable material can be caused by such insufficient light application. In these zones there is a depletion of free radicals where the light has penetrated to only low intensities, such as around the periphery of the light beam. When, at a later moment in time, a light beam of high intensity is moved into position to penetrate these peripheral locations, the source for the production of additional free radicals is limited due to the previous depletion.

There has thus developed a substantial need in the art for a technique and apparatus to overcome the inherent problems with the presently available hardware for photocuring in dental applications. Thus, the typical oral cavity photocure light device which is presently available, has a drop in light flux of 80%, or to 20% of its output at only 1 cm distance, due to the high light ray divergence characteristic of the light beam. Most present photocure light beams must be applied essentially at contact, or not greater than about 2 mm distance from the tooth restorative material, in order to achieve photocuring suitable for dental restorations. The beam sizes typically range between 5 mm and 8 mm in diameter, delivered from fiber optic or quartz rods. In applying such a beam to larger area restorations, such as posterior or cosmetic applications, it is required that the light guide be manually moved near the surface by the operator and, therefore, the end result is a method which is operator technique dependent. Even larger area applicators, which produce 10 mm diameter light beams from optical fibers or the like, require "contact" photocuring, which is extremely cumbersome due to the large size of the applicator which must be applied in the patient's mouth. Larger size light beams could be made available by simply enlarging the dimensions of present devices, but these would be expensive, operationally inefficient and unacceptably heavy and cumbersome. For example, a 10 mm diameter fiber optic light guide is an impractical approach, and would not be an acceptable choice for most dental applications.

SUMMARY OF THE INVENTION

It is an object of this invention to provide an efficient photocuring light source device which overcomes the disadvantages of contact type light apparatus, and enables more reliable curing of photocurable compositions in dental and other applications.

It is another object of this invention to provide visible light curing apparatus which provides a light output which enables a greater depth of cure and, at the same time, enables curing larger size restorations.

It is another object of this invention to provide a visible light curing method which is easily practiced by dentists and which reduces substantially the operator dependent features of prior art techniques.

It is another object of this invention to provide visible light cure apparatus which enables greater access to different portions of the oral cavity, and which enables photocuring of larger size restorations.

It is another object of this invention to provide visible light curing apparatus which overcomes prior art problems of optical collimating, and enables a relatively large beam size without requiring expensive optical components.

It is another object of this invention to provide light source apparatus for dental photocure applications, the apparatus providing a low divergence beam which results in less light scattering when projected onto the target and results in greater light penetration. A further result of greater light penetration is scattering of light within the light sensitive material, enabling curing of shadowed areas.

It is another object of this invention to provide a light source apparatus and method for visible light curing of dental restoratives, wherein the light output can be held a distance away from the dental target, thereby avoiding the prior art problems associated with contact type devices and techniques.

It is another object of this invention to provide a visible light source which outputs a reduced divergence beam, which beam is achieved with relatively inexpensive components.

It is another object of this invention to provide apparatus for generating a reduced divergence light beam for use in dental applications, the apparatus having an optical condensing component which is inexpensive and disposable.

In accordance with the above objects, there is provided apparatus for generating and projecting a relatively large area light beam having a limited divergence, the appartus comprising a source of collimated light operatively coupled into a low angle optical condenser such as a conical reflector or other form of optical condenser, the light output of the condensing means having a beam light divergence substantially less than 30° and typically within 10°. The invention comprises the method of generating said low divergence light beam having a beam diameter of about 1 cm, and directing the beam output from a distance of at least about 1 cm from the dental target, whereby low divergent light is enabled to penetrate over a large target area for curing visible light curable material. In another embodiment, the low visible light source is incorporated into a multifunction operating light apparatus which provides different modes of light output, including a condensed low divergence beam with particular visible light wavelengths filtered out.

DESCRIPTION OF THE PREFERRED EMBODIMENT

Figure 1A:
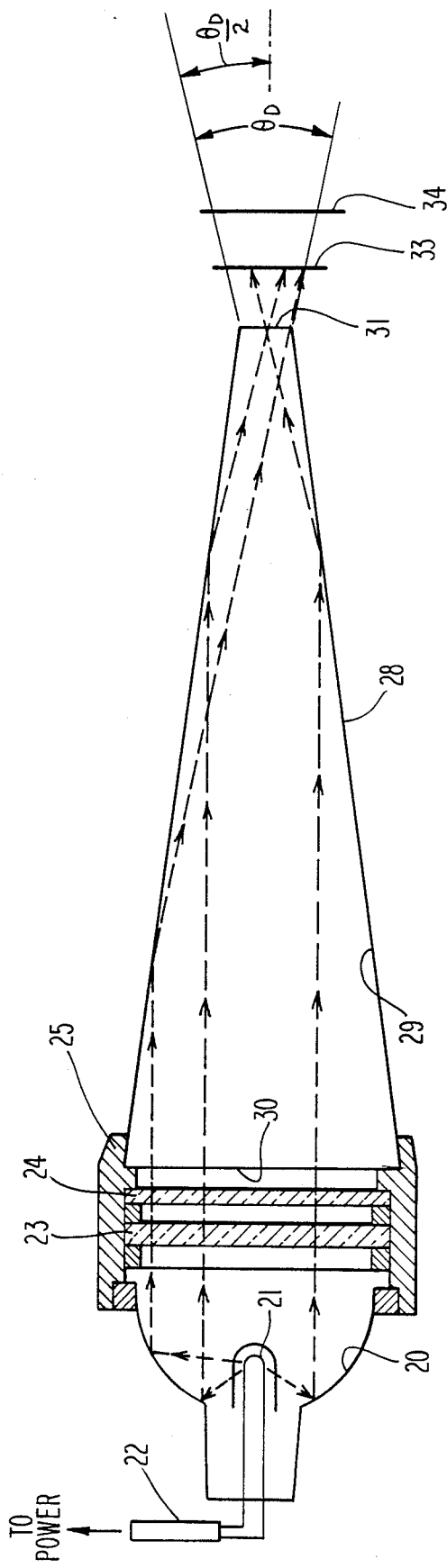
FIG. 1A is a schematic diagram of the basic collimated light source and low angle condensing means, for providing a low divergent light beam output.

Referring now to FIG. 1A, there is shown a schematic diagram of the primary light source apparatus of this invention. A light source is comprised of a bulb, or lamp 21 in combination with a parabolic reflector 20. As is known, when the lamp source is placed at the focal point of the parabolic reflector, and approximates a point source, the reflected light rays are lined up in parallel, i.e. a substantially collimated light beam is generated. Note that light rays which leave the bulb 31 at more than 90° from the optical axis are reflected as part of the beam. It is understood, of course, that a perfectly collimated light beam cannot be achieved, but this simple combination produces a very effective and substantially collimated light beam. The lamp 21, which may be a tungsten halogen lamp or other arc-type lamp, is connected to a suitable power source, not shown, through cable 22. In the preferred embodiment, the lamp has a 41 volt rating, and is operated at about +5% rated voltage.

The light source means further comprises an IR absorbing filter 23, typically 6 mm thick, with an absorption band of 600 nm to 2400 nm. A compound filter 24 may pass visible light wavelengths in the 320–600 nm range and preferably in the 400–500 nm range, and rejects wavelengths in the range of 500 to 800 nm. Filter 24 also reflects wavelengths in the range of 600 to 1000 nm. The filters are mounted to casing 25, suitably made of aluminum. The output surface of the light source means 26 is suitably about 5 cm in diameter.

Also mounted to casing 25, to receive the collimated light beam, is a low angle single continuous condensing element 28, illustrated as a truncated cone. The cone is suitably made of a Mylar backing and has its inner surface 29 coated with an aluminum or other suitable reflective surface material, presenting a reflective condensing surface which reflects the light rays as illustrated. Since the angle of reflection of the light rays is equal to the angle of incidence to the sloping inner surface 29, the maximum angle that a light ray can have at the output 31, or divergence angle, is determined by the angle of convergence of the condensing element, or cone 28. The cone has an output aperture in the range of 3 to −15 mm, preferrably about 1 cm, and is about 6 inches in length. For these dimensions, the angle of divergence, or $\theta_D/2$, is limited to about 10°, i.e. the divergence is $\pm 10\%$. Another way of stating this is that the light beam diverges only about 10° from the optical axis. In practice, the angle of divergence may be in the range of 5° or lower, to about 30°.

The light condensing cone is an effective optical power amplifier, where the ratio of the optical input aperture area to the optical output aperture area is the amplification factor. Thus, the output power is the area ratio times the cone's efficiency factor, times the power input. In the preferred case, for a 5 cm reflector, a 5 cm diameter input aperture and a 1 cm diameter output aperture, the aperture ratio is 25. Typically the efficiency factor is approximately 20%. Thus, for a power input of 200 mw/cm$^2$, the power output is 1000 mw/cm$^2$.

It is to be understood that the condensing means may be other than conical in shape, e.g. pyramidal, etc. As used herein, the term "asymmetrical" means any condensing means that has different size input and output apertures.

For this apparatus, practical light output using a 200 watt lamp with an output aperture 31 that is 1 cm in diameter delivers a light flux of about 1000 mw/cm$^2$. At a 1 cm distance, the light flux in the beam is reduced to about 500 mw/cm$^2$. Directing this large light beam at a posterior, Class IV or an anterior cosmetic application from a distance of 1 cm, eliminates the requirement of mechanical light beam over the object that is to be photocured. This is an equivalent flux density to the Prisma-Lite 5 mm light guide output which is applied at contact. However, in addition to providing light over a larger area, the same flux, with the lower divergence, delivers a greater depth of cure by a factor of 1.7, as applied to light activated materials.

Figure 1B:
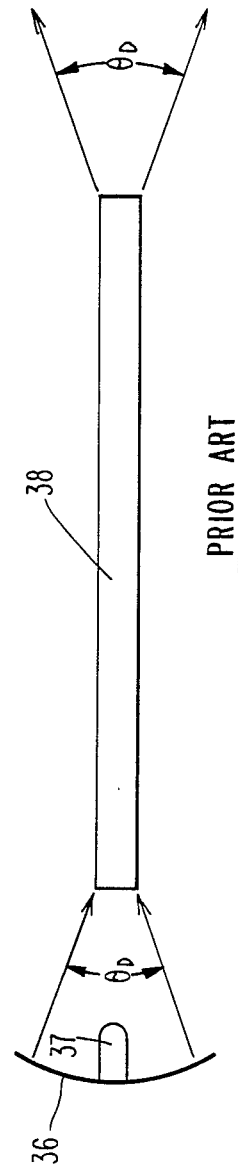
FIG. 1B is a schematic of a prior art arrangement, illustrating a high divergence light output.

Much of the improvement over the prior art is seen by reference to a typical prior art arrangement as shown in FIG. 1B. There, the light source is optically focused by reflector 36, and a light rod 38, or other light transmitting medium is positioned with its input at the focal point. However, when the light is outputted at the other end, it diverges over an angle $\theta_D$, as illustrated. It is to be noted that the angle at which the light rays enter the light guide equals the angle that the light rays exit the light guide, and thus the optical convergence that is achieved at the input is reversed at the output. Even by holding the output of the light guide in contact with the target object, a good percentage of the light is at an angle divergent from the optical axis, with the result that relatively less light is available for penetrating straight ahead. My calculations have shown that, using the invention of FIG. 1, with a light divergence of about 10°, flux applied at a 1.0 cm distance from the cone light output cures to a depth of 1.7 times greater than light applied by conventional photocure hardware applied at contact, where the MW/cm$^2$ (output power) of each is equal. Thus, with this invention not only can a greater depth of penetration be achieved, but the operator dependent inefficiencies caused by contact light curing are avoided.

Figure 2A:
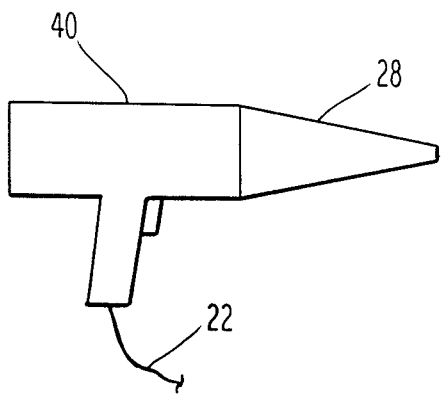
FIG. 2A is a schematic diagram of the low divergence apparatus housed in a hand-held gun housing.

Referring now to FIG. 2A-D, there are shown diagrammatic sketches of various embodiments of the invention. Illustrated in FIG. 2A is the parabolic-cone combination of FIG. 1A, housed in a gun style housing 40. A lead 22 connects the light source to an appropriate power supply. For this proposed embodiment, the cone, or other asymmetrical hollow low angle condensing element 28, may be disposable. Thus, after the dentist has used the cone for treatment of a patient, the cone can be thrown away and another attached to the gun housing for the next use. This is made possible because the Mylar cone as described above is relatively inexpensive when made in large quantities.

Figure 2B:
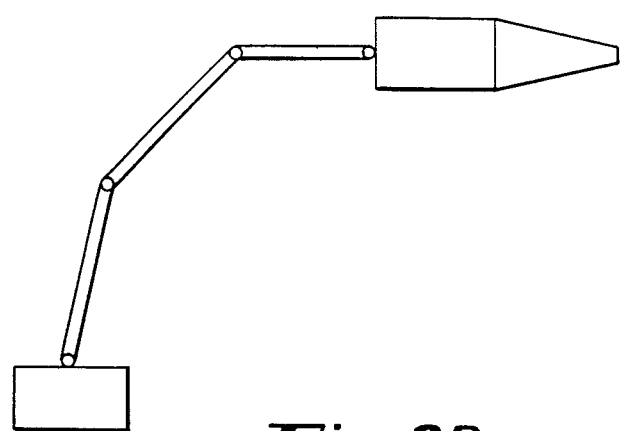
FIG. 2B is a diagrammatic illustration of the low divergence light source being mounted on a manipulable mounting.

FIG. 2B shows the collimated light source-low angle condensing means mounted to a flexible mount, as used frequently in dental applications, to provide a conventional type of arrangement for the dentist's office.

Figure 2C:
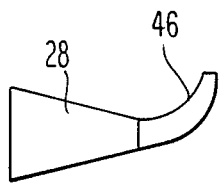
FIG. 2C shows an alternate embodiment of the low divergence optical condenser, whereby the tip is curved so as to provide access to otherwise hard-to-reach dental targets.

In FIG. 2C, there is illustrated another embodiment of this invention, where the low angle condensing means 28 is terminated in a separate end, or tip portion 46, which has a geometry designed to permit dispensing of the light into a posterior or other hard-to-reach locations. Instead of having the cone, for example, end in a truncated aperture, the end portion may be curved at substantially a right angle, such that the optical axis at the output is angularly displaced from the optical axis of main portion of the cone and of the collimated beam. If desired, the main portion 28 of the low angle condensing means may have indents or other means for detachably receiving different end pieces 46, which may be disposable.

In another form, the tip end 46 may be a closed conical configuration with a side light exit port to emit light at about 90° from the optical axis, so as to facilitate directing the output light onto the surfaces of the dental target. The examples of FIG. 2C are illustrative of tip configurations for enabling the dentist to apply light to different targets in restricted locations in the oral cavity.

Figure 2D:
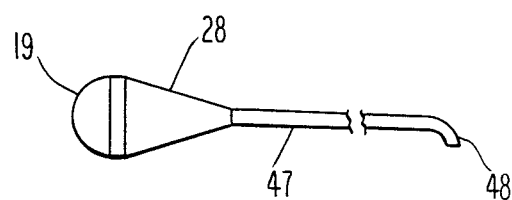
FIG. 2D is an alternate embodiment showing the low divergence light source apparatus outputted into a light guide, for delivery to the dental target at a remote location.

Referring now to FIG. 2D, there is shown a schematic view of another embodiment where it is desired to use a relatively long and flexible light guide means for applying the light directly to the dental target. In this situation, the light source means 19 and condensing means 28 are combined to provide the condensed low divergence light beam. The output of the means 28 is connected directly to a light guide 47 of suitable size, the tip end 48 of which may be easily manipulated by the operator. Although such an embodiment would have the drawback of relatively expensive light guide apparatus, it could be useful where it is desired to have the light source remain fixed in position and have a more conventional output element. It is to be noted that the low divergent beam, in either the configuration of FIG. 2D or the other configurations, is provided without the expensive optics which would otherwise be required in order to form a condensed area collimated beam.

Figure 3A:
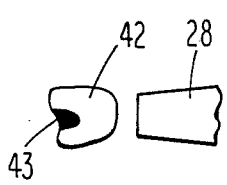
FIG. 3A is a schematic diagram of the method of applying the light beam to penetrate through tooth structure to the target made of restorative material.
Figure 3B:
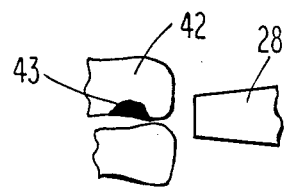
FIG. 3B is another illlustration of the method of this invention whereby the light source output is positioned at a distance from the dental target, illustrating the large beam size relative to the target area, and the ability of the beam to penetrate tooth structure.
Figure 3C:
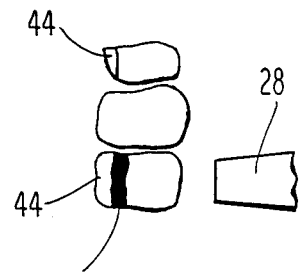
FIG. 3C is another illustration of the method of this invention which is enabled by the efficiency of the apparatus.

Referring now to FIGS. 3A-3C, there are shown sketches of applications of the method of this invention, particularly illustrating the advantages of utilizing a beam having a diameter of at least about 1 cm for photocuring restorative materials in a patient's oral cavity. As seen in FIG. 3A, the output aperture 31 is displaced from the outer surface of the tooth 42. As illustrated, the cavity which has been filled with a restorative material, at 43, is at an interior position, such that the light has to penetrate through tooth structure. With the increased penetrating capability of this invention, this is efficiently done. Likewise, in FIG. 3B, there is shown another example of displacing the output aperture 31 from both the tooth surface 42 and the interior restorative material 43. In FIG. 3C, there is shown a schematic illustration of a bridge network, wherein a metal brace 44 is used, behind which is restorative material 43. Due to the presence of the opaque metal, the light must be incident from the other side, such that it must penetrate a relatively great depth through the tooth structure. This is much more adequately handled with the apparatus and technique of this invention, compared to the prior art.

Figure 4:
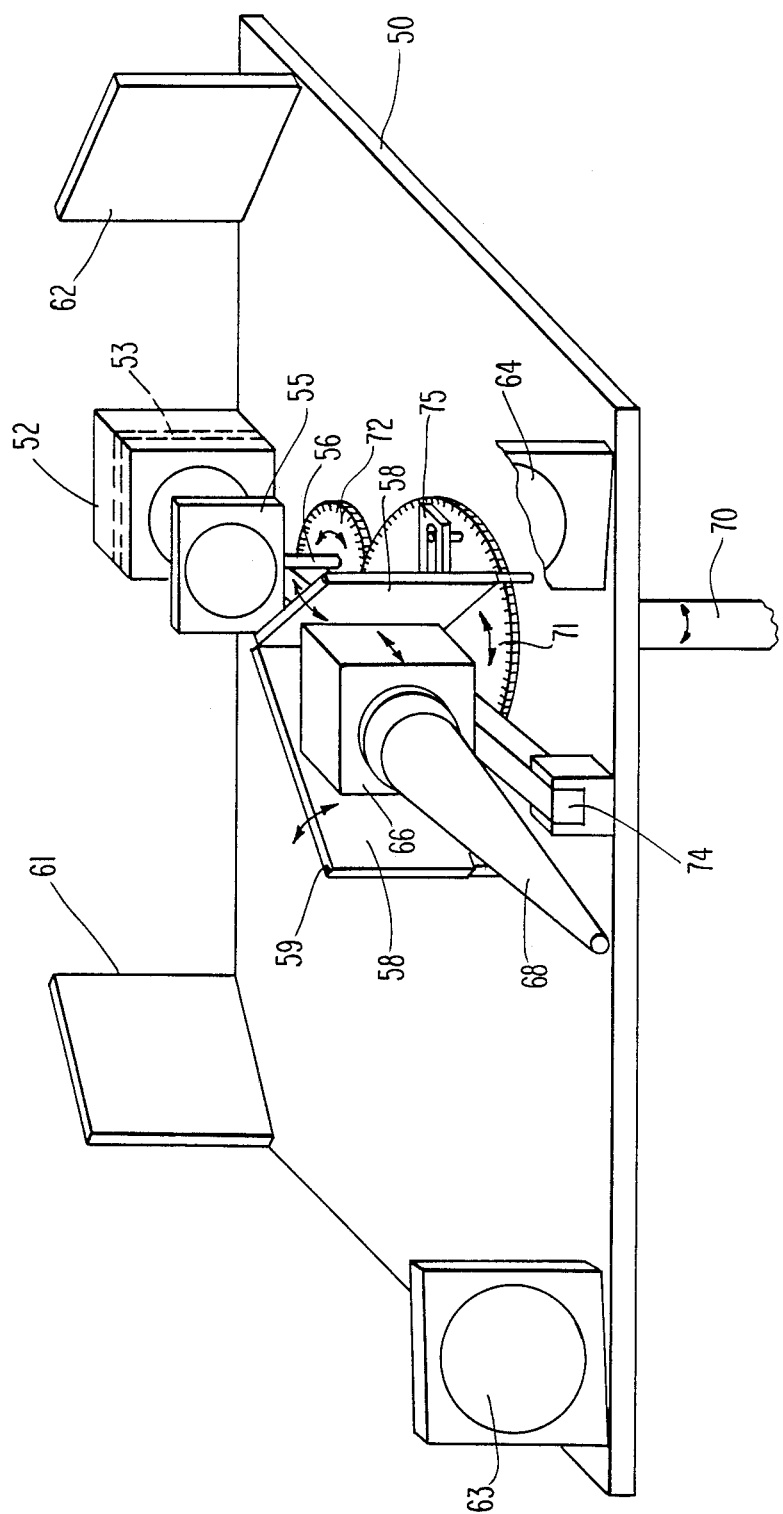
FIG. 4 is a schematic illustration of an optical system enabling different modes of light output, which system includes the embodiment of FIG. 1.

Referring now to FIG. 4, there is shown another embodiment of this apparatus wherein the parabolic reflector-cone condensor combination is combined with other apparatus to comprise a multi-light mode dental apparatus. The optical components of the system are mounted on a platform or other support means 50, which in turn may be flexibly mounted by means not shown. Lamp housing 52 comprises a lamp with a parabolic filter, as illustrated in FIG. 1A, for producing a collimated beam with an output diameter of about 2⅜ inches. Housing 52 also contains an IR absorbing filter illustrated at 53. Directly in the path of the output of the collimated beam is a rotatable notch filter, which is a rejection filter for filtering out the wavelengths of about approximately 400–500 nm. This filter is rotatable on a pivot 56. Alternately, the notch filter may be mounted so as to be indexed into position from the side, permitting mount 66 to be moved into close proximity to lamp 52. A pair of reflectors 58 are rotatable on pivot arms 59, and are normally in position to reflect the light beam toward the pair of fixed reflectors 61, 62. These reflectors in turn direct output beams through optional lenses 63 and 64 respectively. By this means, a pair of displaced light sources are provided, for general lighting purposes.

A cone mount 66 is provided, which houses a band-pass filter 67, which passes light in the visible light range. Extending from mount 66 is a disposable reflecting cone 68, such as illustrated in FIG. 1. When it is desired to output light from the cone 68, it is necessary to rotate reflectors 58 out of the way, and move the cone toward the lamp, so that is can efficiently collect the collimated beam coming from lamp housing 52. This is dome by utilization of elements 70–75, as is seen be reference to both FIGS. 4 and 5, and as discussed in the following paragraph.

When the operator wants to change the light mode, this is done by rotating mode indexing handle 70, which in turn rotates gear 71. Gear 71 meshes with gear 72, which turns pivot arm 56 and notch filter 55. When filter 55 is rotated 90° with respect to the position illustrated, it is effectively removed from blocking any substantial amount of the light beam. Also, the cone mounting 66 and cone are moved toward the lamp housing 52 by the operation of pin 73, arm 75 and linear slide 74. As seen more clearly in FIG. 5, arm 75, which is connected to the linear slide 74, which in turn carries housing 66, has a linear slot within which pin 73 is positioned. As wheel 71 is turned in a counterclockwise direction, the pin carries slide 74 and mount 66 back toward housing 52, pushing open the rotatable reflectors 58. Filter 55 is also rotated, so that visible light passes. Alternately, notch rejection filter 55 can be moved into or out of position independently, by means not shown, to change the wavelength characteristics of the illumination light.

There have thus been illustrated several embodiments of the apparatus and method of this invention. A key feature of the invention is the provision of a light beam with a low angle of divergence. As used herein, the term "angle of divergence" refers to the angle within which substantially all of the light is contained. Thus, a beam with a light divergence limited to 10° is a beam within which substantially all of the flux is no more than 10° from the optical axis. Practically, as is known, it is impossible to sharply limit divergence to any given angle, just as it is practically impossible to generate a perfectly collimated beam in the first instance. However, for example, a beam with light divergence limited to ±X° is one that has at least 80 to 90% of its light flux within ±X° of the optical axis.

As used in this specification and the claims appended hereto, the phrase "low angle light condensing means" refers to a hollow asymmetrical element, such as a truncated cone or pyramid, having a reflective interior, and having a shallow angle of convergence from the larger input aperture to the smaller output aperture. The use of such a low angle condensing means in combination with a collimated beam light source enables relatively inexpensive apparatus for production of an output beam with a limited light divergence. As used herein, the term "low light divergence" or "limited light divergence" means less than 30°. It is to be understood that a cone of smaller length than the 6 inch cone illustrated, or a cone of similar length but smaller output aperture, could be used to provide a beam with a divergence of more than 10°, but still less than prior art light sources. Although in the preferred embodiment the beam is limited to about 10° divergence, the invention embraces any such apparatus and method utilizing an output beam with a divergence ranging from almost nothing, e.g., 3° or less, up to about 30°.

Figure 5:
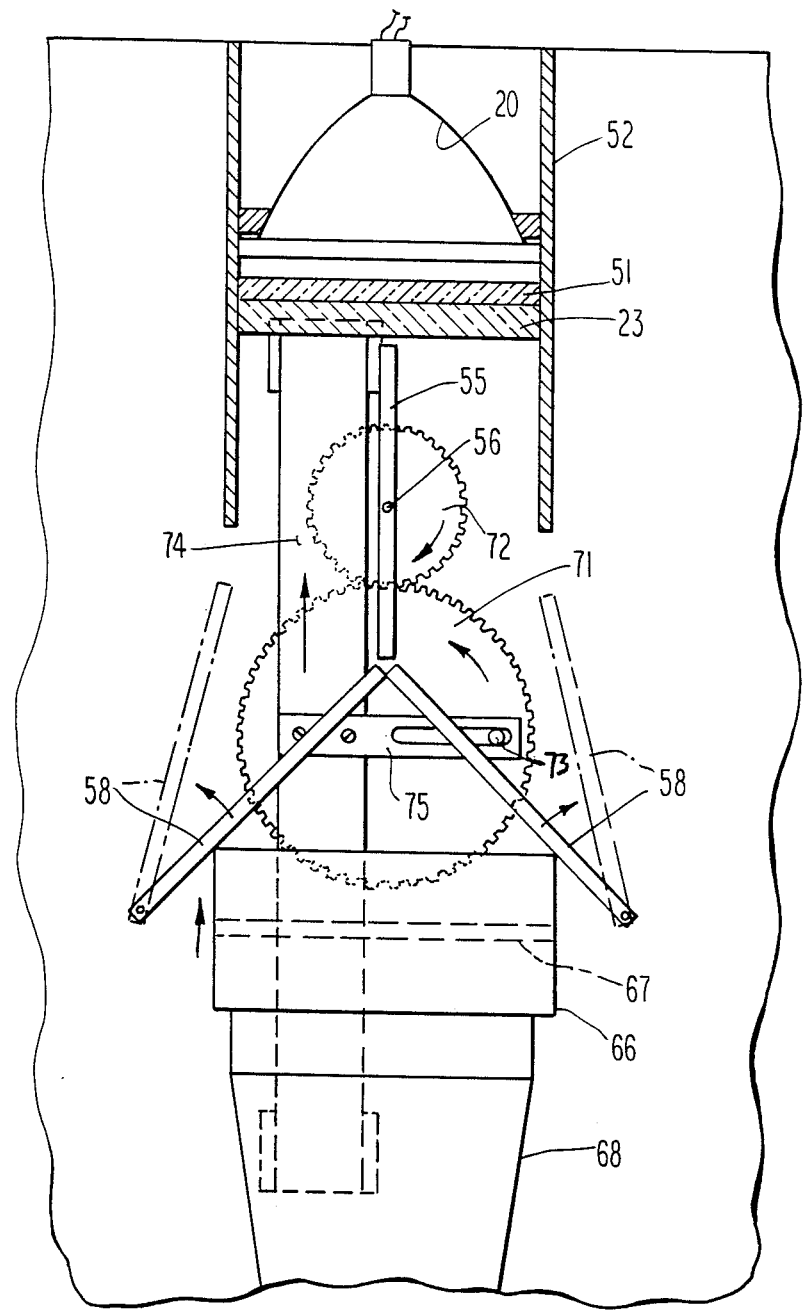
FIG. 5 is a plan sectional view of a portion of the apparatus of FIG. 4, illustrating the means for changing the mode of operation.

In practice, the apparatus and method of this invention provides optimum facility to the dentist for using light curable materials. The apparatus disclosed in FIGS. 4 and 5 provides an illumination source of substantially white light, when the notch filter is removed from the beam path, which white light can be used for illumination of the mouth and preparation of the desired location within the patient's mouth for receipt of the light curable material. When this step is completed, the dentist inserts the notch filter, thereby providing illumination with substantially yellow light. In the presence of the yellow light illumination, the dentist places the light curable material at the desired target location and forms it. When that step is complete, the dentist then uses the portion of the apparatus for generating the low divergence collimated light beam, which is applied to the dental target as described hereinabove.

In summary, there is provided an improved apparatus, for generating a low divergence light beam, and a method of utilizing same. The collimated beam has improved penetrating characteristics for penetrating natural tooth structure, glass, glass ceramics, clear and translucent plastics, and other translucent materials. The light beam may be reduced in size as desired or, alternately, may be larger than conventional beams used for dental applications, thereby enabling less operator-dependent operations.

I claim:

1. A method of visible light curing of light curable material in a dental environment, comprising generating a low divergence collimated light beam and directing said light beam on a predetermined target area in a patient's mouth so that said light reaches pre-positioned light curable material.

2. The method as described in claim 1, comprising generating said light beam to have a divergence of less than about 30°.

3. The method as described in claim 1, comprising generating said light beam with apparatus having a beam output aperture to provide a beam of at least 1 cm in diameter, and positioning said output aperture at least about 1 cm from said target area.

4. The method as described in claim 1, comprising directing said light beam through natural tooth structure to cure light curable restorative material.

5. The method as described in claim 1, wherein said collimated light has a diameter of at least 1 cm, and directing said light so as to simultaneously cure visible light curable material positioned in two or more teeth at a time.

6. The method as described in claim 1, comprising directing said light beam through dental materials consisting of glass, glass ceramics, and clear and translucent plastics.

7. The method as described in claim 1, wherein the step of generating comprises limiting the divergence of said collimated light beam to about 10°.

8. The method as described in claim 9, wherein the step of generating a collimated low divergence light beam comprises limiting said divergence to less than 30°.

9. A method of applying a light curable material in a location within an oral cavity, comprising illuminating the oral cavity with substantially white light and preparing said location for application of said material, illuminating the oral cavity with yellow light and placing and forming said material at said location, generating a collimated low divergence light beam comprising wavelengths for curing said material and directing said generated collimated light beam on said placed and formed material.

10. The method as described in claim 9, wherein said generated light beam comprises wavelengths in the range of about 400 nm–500 nm.

11. The method as described in claim 9, comprising directing said generated light beam from a source having an output aperture, and positioning said output aperture at least about 1 cm from the outside surface of said location.

* * * * *